United States Patent [19]

Cohen et al.

[11] Patent Number: 5,146,009
[45] Date of Patent: Sep. 8, 1992

[54] PROCESS FOR THE RECOVERY OF ALCOHOLS USING AN ORGANIC ACID-MODIFIED POLYMER MEMBRANE

[75] Inventors: Abraham D. Cohen, Sarnia, Canada; William D. Diana, Belle Mead; James J. Baiel, Morris Plains, both of N.J.

[73] Assignee: Exxon Chemicals Patents Inc., Linden, N.J.

[21] Appl. No.: 323,081

[22] Filed: Mar. 13, 1989

Related U.S. Application Data

[63] Continuation of Ser. No. 9,795, Feb. 2, 1987, abandoned.

[51] Int. Cl.$^5$ .............. C07C 29/12; C07C 31/10; C07C 31/12; C07C 31/125
[52] U.S. Cl. .............. 568/889; 568/886; 568/888; 568/913; 568/916
[58] Field of Search .......... 568/888, 889, 916, 886, 568/913; 560/248

[56] References Cited

U.S. PATENT DOCUMENTS

| | | | |
|---|---|---|---|
| 2,945,891 | 7/1960 | Van Heel | 568/888 |
| 3,035,060 | 5/1962 | Binning et al. | 568/913 |
| 3,062,905 | 11/1962 | Jennings et al. | 568/913 |
| 3,193,582 | 7/1965 | Adams et al. | 568/913 |
| 3,479,390 | 11/1969 | Blatz et al. | 560/265 X |
| 3,950,247 | 4/1976 | Chiang et al. | 568/913 |
| 4,065,512 | 12/1977 | Cares | 568/899 |
| 4,520,213 | 5/1985 | Victor | 568/913 |
| 4,532,347 | 7/1985 | Vaughn | 560/265 X |
| 4,538,010 | 8/1985 | Diana | 568/918 |

FOREIGN PATENT DOCUMENTS 0827474 5/1981 U.S.S.R. .............. 568/913

OTHER PUBLICATIONS

I. Cabasso et al., "The Permselectivity of Ion-Exchange Membranes for Non-Electrolyte Liquid Mixtures. I. Separation of Alcohol/Water Mixtures with Nafion® Hollow Fibers," *J. Membrane Sci.* 24, 101-119, 1985.

M. L. Langhorst, "A Hollow Fiber Device for Separating Water Vapor from Organic Vapors", *Am. Inc. Hyg. Assoc. J.*, 44, 592, Mar. 1983.

I. Cabasso, "Organic Liquid Mixture Separation by Permselective Polymer Membranes. 1. Selective and Characteristics of Dense Isotropic Membranes Employed in the Pervaporation Process," *Ind. Eng. Chem. Prod. Res. Dev.*, 22, #2, 313 (1983).

Hsu and Gierke, *J. Membrane Science*, 13, 1983, 307-326.

S. C. Stinson, "Electrolytic Cell Membrane Development Surges", *Chemical and Engineering News*, Mar. 15, 1982.

Y. Yamabe, "Perfluorinated Ionomer Membranes," *Kirk-Othmer Encyclopedia of Chemical Technology* (Supplement to 3rd Ed.), John Wiley & Sons, New York, New York (1984).

T. D. Gierke, G. E. Munn and F. C. Wilson, "Morphology of Perfluorosulfonated Membrane Product", pp. 195-216, *Perfluorinated Ionomer Membranes*, ed. A. Eisenberg and H. L. Yaeger, ACS Symp. Series 180 (ACS, Washington, DC (1982).

S. J. Sondheimer et al., *Rev. Macromol. Chem. Phys.*, C26 (3), 353-413 (1986).

Abstract, Par. 5, Techgram Japan, Chemtech Oct. 1985, p. 605.

*Primary Examiner*—Vivian Garner

[57] ABSTRACT

According to the process of this invention, alcohols are recovered from aqueous acid solution by permeation of the alcohol through an organic-acid modified polymer membrane. An improved process for the manufacture of alcohols by acid absorption of olefins is also disclosed, the improvement residing in the use of an organic-acid modified polymer membrane to selectively permeate alcohols from the concentrated aqueous strong acid solution thereof co-produced in their synthesis from olefins.

22 Claims, 4 Drawing Sheets

PROCESS FOR THE RECOVERY OF ALCOHOLS USING AN ORGANIC ACID-MODIFIED POLYMER MEMBRANE

CROSS-REFERENCE TO RELATED APPLICATION

This application is related to our co-pending application, Ser. No. 07/009,794, filed Feb. 2, 1987, now abandoned, which was refiled as Ser. No. 07/320,903, filed Mar. 7, 1989, now U.S. Pat. No. 4,876,403, entitled "Process for the Recovery of Alcohols Using a Perfluorinated Ionomer Membrane".

BACKGROUND OF THE INVENTION

1. Field of the Invention

This application relates to a new and novel process for recovering alcohols from aqueous strong acid streams. More particularly, the present application describes a process for the separation of alcohols from aqueous acid solution by permeation of the alcohol through a selectively permeable membrane comprising an organic acid-modified polymer.

2. Description of the Prior Art

The large-scale manufacture of alcohols from olefins is of considerable importance both for the alcohol produced and as a pathway in other processes. Isopropyl alcohol (IPA), for example, which is manufactured from propylene, is used as an ethanol denaturant and a solvent as well as in the production of acetone by catalytic dehydrogenation. Sec-butyl alcohol (SBA), obtained from butylenes, is used predominantly in the production of methyl-ethyl-ketone (MEK) by dehydrogenation.

The conventional method of obtaining alcohol from the corresponding olefin is by absorption of gaseous olefin (or "extraction" of liquid olefin) (the term "absorption" will be understood to refer hereinafter to both processes) in an aqueous solution of strong acid, typically sulfuric acid. This process comprises two steps: sulfuric acid-catalyzed esterification of the olefin to give a stream identified as sulfuric acid extract (SAE) which comprises the mono-and di-alkyl esters of sulfuric acid corresponding to the olefin used, some alcohol, sulfuric acid, hydrocarbon by-product and unreacted olefin; and hydrolysis of the sulfated ester to give alcohol and sulfuric acid.

For example, the absorption of butene in the membrane with sulfuric acid to form sec-butanol and the sec-butyl ester of sulfuric acid can be illustrated by the following equation:

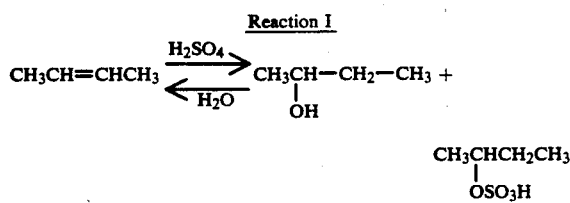

Reaction I

Thereafter, water is admixed with the SAE as it is withdrawn from the absorber in order to hydrolyze the ester and to facilitate alcohol recovery by steam stripping. There is thereby produced a diluted sulfuric acid stream which must for economic reasons be treated to concentrate it with respect to its sulfuric acid content, after which it is recycled to the olefin absorption step.

While it is also known to obtain alcohols by means of direct catalytic hydration, this process has the disadvantage of being equilibrium constrained, thus requiring olefin feeds of high purity.

Of course, other alcohols may be produced by absorption of olefins in acid, generally comprising saturated mono-alcohols having from 2 to 8 carbon atoms per molecule, and preferably having 3 or 4 carbon atoms per molecule. Examples of such alcohols are ethanol, iso-propanol, iso-butanol, sec-butanol, the pentanol isomers, etc., preferably the propanol and butanol isomers, most preferably isopropyl alcohol and sec-butyl alcohol.

Steam stripping the SBA and reconcentrating the spent sulfuric acid by distillation are both energy intensive processing steps. For example, there is an energy toll of about 1 to 2 lbs. steam/lb. alcohol product obtained in the steam stripping of the sulfuric acid extract, about 1 to 2 lbs. steam/lb. alcohol obtained, for reconcentrating the acid; and about 2 to 3 lbs. steam/lb. alcohol product obtained for, e.g., SBA distillation. Therefore, it will be apparent that means for recovering the alcohol product from the sulfuric acid stream at reduced energy cost would constitute a significant improvement over conventional practices in the manufacture of alcohols by absorption of olefins in acid.

Further, many lower molecular weight alcohols are totally miscible with and form azeotropes with water. Azeotropes at the azeotropic point give vapor of the same composition as the azeotropic liquid and thus cannot be further concentrated by normal distillation no matter how efficient the fractionating column used. Thus an alternative means to effect separation of such mixtures is highly desirable.

Various means have been suggested for improving the efficiency of such a process. U.S. Pat. No. 4,538,010, for example, describes an improved process for recovery of alcohols from the concentrated aqueous strong acid solution co-produced in their synthesis by acid absorption of olefins, the improvement residing in the use of a carboxylic acid extraction solvent to recover the alcohol from the strong acid extract, the resulting carboxylic acid extract phase being substantially free of water or strong acid. A heavy phase comprising substantially reconcentrated strong acid solution containing alkyl moieties is thereby also formed, which is suitable for recycle directly to the absorber. While the energy costs associated with acid reconcentration are thereby reduced relative to conventional processes, the large volumes of carboxylic acid extract required in the process introduce difficulties in handling as well as the added expense of the extraction solvent itself.

It is known in the art that certain membranes are permeable to molecules containing hydroxyl groups, such as water and aliphatic alcohols, and that certain of these membranes selectively permeate water over alcohols from solution containing the two. For example, U.S. Pat. No. 3,950,247 and 4,199,445 (the latter having issued on a divisional application based on the '247 patent), disclose a process for dehydrating aqueous solutions containing soluble organic or inorganic compounds by contacting the mixture against one side of an organic polymer membrane of polyvinyl chloride or having active anionic groups derived from strong acids, and withdrawing at the second side a mixture in the vapor phase having increased water concentration relative to the feed. Notably, in Example 1, a copolymer of styrene and acrylic acid is used to concentrate a formalin solution containing about 37% formaldehyde, 53% water, 0.05% formic acid (pKa=3.75), and 10% methanol, by selectively permeating water along with the formic acid. Thus, it is taught to use an organic polymer membrane to remove acid and water from a solution also containing alcohol and formaldehyde. In Example 7, where a sulfonated ethylene membrane was used to dewater a three-component system containing water, methanol and formaldehyde, but not acid, the order of selectivity was determined to be water>methanol>-formaldehyde. Finally, Example 18 teaches dewatering of alcohol solutions, including azeotropic mixtures, by preferential permeation of water through certain organic polymer membranes.

It is further known that certain perfluorinated ionomer membranes with pendant sulfonate groups in the hydrogen or cationated form are permeable to molecules containing hydroxyl groups, such as water and aliphatic alcohols. In Examples 14, 15 and 16 of U.S. Pat. No. 4,199,445, nitric acid solution is concentrated by permeation of water through polymer membranes containing sulfonic acid groups, including the XR membrane of DuPont, which is a sulfonated perfluorinated polymer. Cares, U.S. Pat. No. 4,065,512, teaches dehydration of t-butanol by contacting with a perfluorosulfonate acid resin while passing dry fluid on the other side of the membrane, thereby removing the water of dehydration through the membrane. Cabasso et al. describe the separation under pervaporation conditions of alcohol/water vapor mixtures by Nafion 811 hollow fiber membranes, the water preferentially permeating through the membrane (I. Cabasso et al., "The Permselectivity of Ion-Exchange Membranes for Non-Electrolyte Liquid Mixtures. I. Separation of Alcohol/Water Mixtures With Nafion Hollow Fibers," *J. Membrane Sci.* 24, 101–119, 1985). The permeability of perfluorinated ionomer membranes has also been used to advantage to separate water vapor from hydrocarbons, M. L. Langhorst, "A Hollow Fiber Device for Separating Water Vapor from Organic Vapors", *Am. Ind. Hyg. Assoc. J.*, 44, 592, March, 1983, and alcohols from hydrocarbons, I. Cabasso, "Organic Liquid Mixture Separation by Permselective Polymer Membranes. 1. Selective and Characteristics of Dense Isotropic Membranes Employed in the Pervaporation Process," *Ind. Eng. Chem. Prod. Res. Dev.*, 22, #2, 313 (1983). In Vaughan, U.S. Pat. No. 4,532,347, oxygenated hydrocarbons such as alcohols are removed from fluid mixtures by permeation through a perfluorinated membrane with an extracting solvent containing a reactant which by reacting with the hydrocarbons maintains a high concentration gradient of the hydrocarbon across the membrane.

SUMMARY OF THE INVENTION

It has been found that alcohol can be recovered from an aqueous acid feedstream by contacting the feedstream against one side of a selectively permeable membrane comprising an organic acid-modified polymer and withdrawing at a second side of the membrane a permeate comprising alcohol in increased concentration relative to the feed mixture. An "organic acid-modified" polymer is herein defined as a polymer which has been contacted with an organic acid under contacting conditions effective to bring about absorption of the acid by the polymer.

It is therefore an object of this invention to disclose a process for separating alcohol from an aqueous acid feedstream by contacting the feedstream against a selectively permeable membrane comprising an organic acid-modified polymer and by withdrawing at a second side of the membrane a permeate comprising alcohol in increased concentration relative to the feedstream.

It is another object of this invention to disclose an improved process for the recovery of alcohols from the aqueous strong acid solution co-produced in their synthesis by acid absorption of olefins.

It is a further object of this invention to obtain alcohols by acid absorption of olefins at reduced energy cost relative to conventional processes, by use of such a membrane.

It is still a further object of this invention to describe a process for producing alcohol by acid absorption of olefins wherein by use of such a membrane, acid reconcentration is accomplished without distillation.

It is an even further object to employ a membrane characterized by selectivity values with respect to the components of the aqueous strong acid solution such that alcohol and sufficient water permeate the membrane, so that there is thereby also recovered at the feed side of the membrane an acid solution which is reconcentrated with respect to acid content to a concentration suitable for direct recycle in the process.

It is an even further object to describe a continuous process for the manufacture and recovery of alcohols by use of such a membrane, wherein permeation of the alcohol through the membrane provides the driving force for continuous formation of the alcohol product.

DETAILED DESCRIPTION OF THE INVENTION

Prior Art Methods

Figure 1:
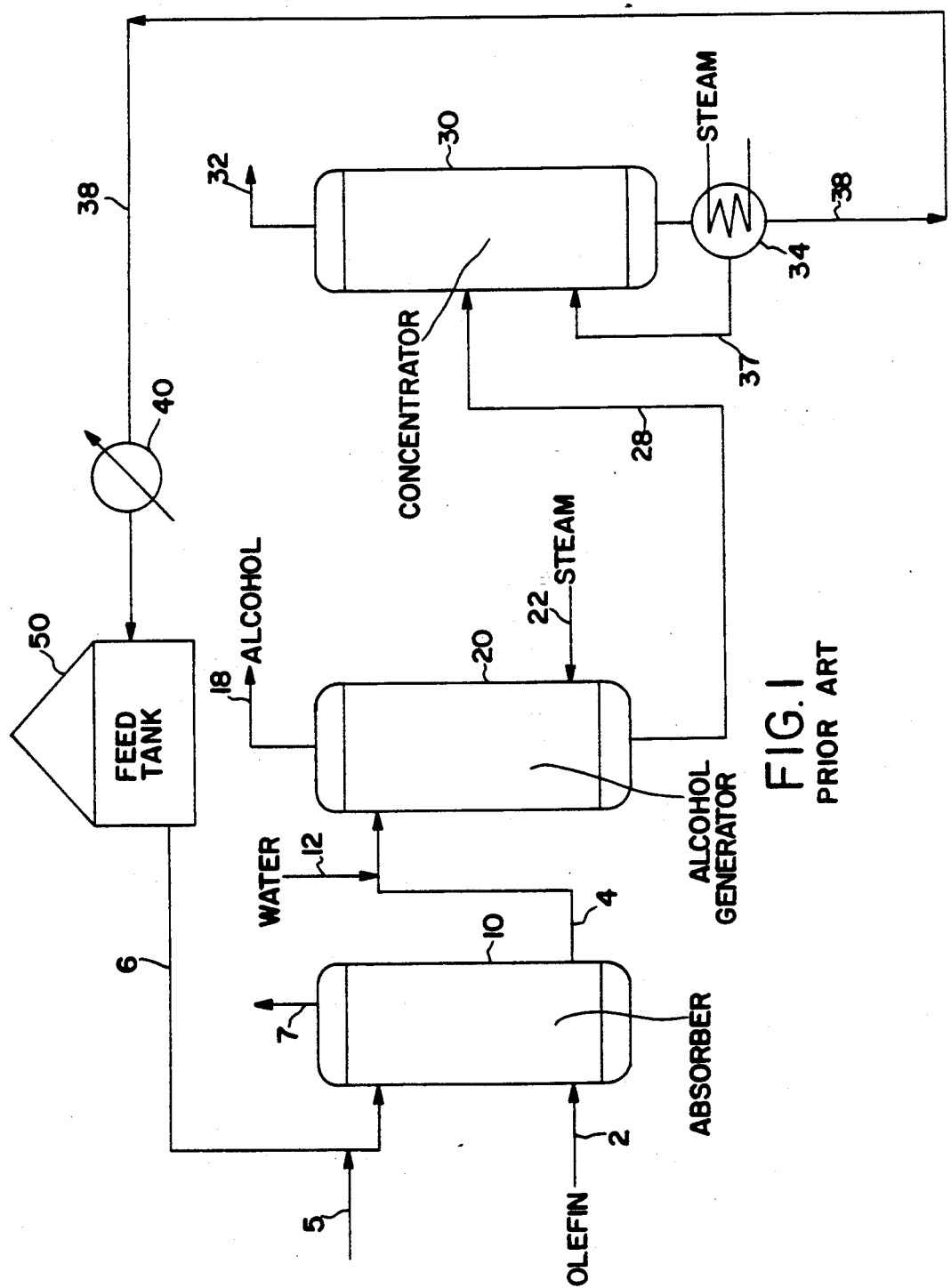
FIG. 1 is a diagrammatic illustration of a prior art process for recovery of alcohols from olefins by sulfuric acid-catalyzed hydration of the olefin, dilution of the sulfuric acid extract and steam stripping of the diluted acid extract for recovery of the alcohol vapors.

The commercial manufacture of alcohols by absorption of olefins in acid typically proceeds as illustrated in FIG. 1. Olefin feed is passed as a gas (or liquid) via line 2 to an absorber 10 wherein it is contacted with and absorbed by a concentrated aqueous strong acid stream introduced via line 6, to form the corresponding alcohol and alkyl ester of the strong acid.

The olefins to be hydrated can be obtained from any available source, such as the destructive distillation of carbonaceous materials, but particularly from the cracking of petroleum hydrocarbons such as is practiced in the petroleum refining of mineral oils. The olefin can also be conventionally obtained by careful fractionation of cracked petroleum gases and is preferably substantially free of higher unsaturates, particularly diolefins such as butadiene, etc. Illustrative of olefins which are employed are lower branched and straight-chain alkenes (i.e., alkenes of 2 to 6 carbon atoms), such as ethylene, propylene, the butylenes and the like.

The strong acid used to absorb the olefin (also termed "olefin hydration acid") generally comprises a strong organic or inorganic acid which is miscible with water and which is characterized by dissociation constants ("pK" values) in aqueous solutions of less than about 3.5. Examples of suitable inorganic olefin hydration acids are hydrofluoric acid, hydriodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like.

For convenience, the following discussion will be directed to the use of sulfuric acid, although it will be understood that any of the above strong acids can also be employed.

The aqueous concentrated acid stream 6 which is used to absorb the selected olefin feed is a concentrated acid stream whose precise acid concentration will vary depending on the olefin which is employed, the strong acid selected, the temperatures of reaction and other conditions: For example, when sulfuric acid is used as the strong acid, stream 6 will generally contain from about 45 to 85% acid strength sulfuric acid for hydration of propylene and from about 45 to 75% acid strength sulfuric acid for reaction with butylene or higher olefin feeds.

The temperature and pressure employed in absorber 10 generally also vary depending on the olefin, the acid concentration and other factors. Generally, a temperature of from about 20° to 150° C. is used, and the pressure is sufficient to maintain the desired phases in the absorber. Typically, for example, propylene is absorbed from a gas phase at a temperature of from about 90° to 150° C., and at a pressure of from about 100–500 psig.

As illustrated, the olefin and sulfuric acid streams are contacted in a counter-current fashion with the sulfuric acid stream being introduced into the upper portion of the absorber 10. Unabsorbed gases are withdrawn from the upper portion of absorber 10 via conduit 7 and can be concentrated and recycled, if desired, to conduit 2 or subjected to conventional scrubbing/washing treatment, as with caustic solutions, and vented from the process. The resulting sulfuric acid extract which is withdrawn as a liquid product via line 4 from the lower portion of absorber 10 contains water, sulfuric acid (generally in concentration of about 35 to 65 wt. %), and preferably from about 45 to 55 wt. % absorbed olefin values. The term "absorbed olefin values" is intended to refer to all molecules in the liquid which contain alkyl moieties corresponding to the olefin used, such as alkyl esters of sulfuric acid, free alcohol and free di-alkyl ether. The concentration of the alkyl ester in stream 4 can vary widely, and is generally from 15 to 30 wt. % of the total alkyl ester (mono- and di-alkyl ester), in the case of lower alkenes (e.g. propylene and butylene) absorption. For example, in the case of propylene, free isopropyl alcohol is generally present in the extract in an amount of from about 10 to 45 wt. %. The extract can also contain free di-isopropyl ether, which if present will be generally in a concentration of less than about 15 wt. %, preferably from about 3 to 6 wt. %. (Weight % propylene values are calculated and reported herein on the basis of $C_3H_6$ moieties.)

Good contact between the olefin, or the mixture containing it, and the absorbing acid is important. This may be achieved, for instance, by efficient agitation or by the use of absorption towers, preferably in countercurrent flow. The absorption may be continued, if desired, until the concentration of olefin in the gaseous effluent from the absorbing zone has been reduced to below about 5% by weight, and it will therefore be understood that olefin of any concentration higher than 5% in the feed can be treated.

The extent of absorption in a countercurrent system such as a series of agitator vessels and intermediates separators will depend not only on the relative amount of acid employed, but also on the length (number of stages) and capacity of the system and on the rate of throughput. Mixtures of relatively low olefin content will require a greater number of stages under otherwise similar conditions to obtain a given degree of absorption.

In the second stage of the hydration process, water is conventionally added via line 12 to the absorber product stream 4 for hydrolysis of any alkyl ester to form additional quantities of the corresponding alcohol, e.g., isopropanol from mono- or di- (isopropyl) sulfate. The manner in which the water and absorber product stream are contacted varies, and the art employs a variety of such methods, including (1) in-line addition of water (as illustrated), with a provision for a suitable length of conduit to provide adequate mixing and reaction time, and (2) contacting of the absorber product stream and water in a separate reaction vessel with agitation (not shown).

The amount of water which is added to the absorber product stream also varies widely. Generally, in conventional processes sufficient water is added in order to reduce the acid strength to from 45 to 55 wt. % acid strength sulfuric acid. These reduced acid strengths are desired to permit subsequent recovery of the alcohol by steam stripping of the alcohol-containing aqueous acidic extract.

The diluted sulfuric acid stream thus formed is generally at 45 to 55 wt. % acid strength, and is then passed via line 4 to distillation column 20, herein termed the "alcohol generator", wherein crude alcohol is recovered as an overhead product via line 18 by steam stripping. The overhead alcohol product can then be passed to further conventional processing to produce alcohol of the required purity.

A bottoms product is withdrawn from alcohol generator 20 via line 28 and comprises a sulfuric acid stream which generally contains from about 40 to 60 wt. %, and preferably from about 45 to 55 wt. % acid strength sulfuric acid.

In conventional processes, the alcohol generator bottoms 28 are passed directly to another distillation column 30, hereinafter termed the "acid concentrator", wherein the acid stream is distilled (e.g., by use of a steam heat exchanger 34 and reboiled stream 37) for removal of water as overhead 32 and to form a second bottoms product 38 comprising a reconcentrated acid stream. These concentrated bottoms are generally cooled in cooler 40 and passed to storage tank 50 for ultimate recycle to the absorption step 10, with addition of make-up acid 5, as required.

PRESENT INVENTION

It has been found that alcohols can be recovered from an aqueous acid feedstream by contacting the feedstream against one side of a selectively permeable membrane comprising an organic acid-modified polymer and withdrawing at a second side of the membrane a permeate comprising alcohol in increased concentration relative to the feedstream.

This process may be used to advantage in the recovery of alcohols from the aqueous strong acid extract co-produced in their synthesis by acid absorption of olefins.

It is contemplated that this process may be further used to advantage in an alcohol manufacture and recovery process in combination with one or more membranes known to the art, to provide an alcohol recovery and acid reconcentration system which enables substantial energy savings relative to conventional processes.

The "organic acid-modified" polymer membranes of the present invention comprise organic polymers, copolymers or mixtures thereof, which have been contacted with an organic acid under conditions of contacting effective to bring about absorption of the acid by the polymer.

Membranes effective in the process of present invention comprise organic polymers which have been modified by contacting with an organic acid selected from the group consisting of alkyl carboxylic acids having from 6 to 20 carbon atoms per molecule. These acids therefore comprise at least one member selected from the group consisting of carboxylic acids of the formula:

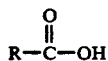

wherein R is an alicyclic or acyclic alkyl group having from 5 to 19 carbon atoms. When "R" is acyclic alkyl, the alkyl group can be straight or branched chain. The "R" group can be substituted with nonreactive groups such as fluoro and chloro. Examples of such "R" groups are pentyl, hexyl, decyl, dodecyl, tetradecyl, undecyl, 2-ethylhexyl, cyclohexyl, cyclooctyl, and fluoro- and chloro-substituted derivatives of the foregoing.

Preferred carboxylic acids comprise 14 to 20 carbon atom carboxylic acids where R is not a straight chain acid. Examples of such carboxylic acids are isostearic acid and neo-decanoic acid.

Suitable carriers which may be used as membranes either as polymers, copolymers or mixtures thereof are characterized by stability in strong acid environment and by the ability to absorb the aforementioned carboxylic acids when contacted with the acids under suitable conditions of contacting. Further, these membranes must be able to form or retain their structure as a coherent film when used in the process of the present invention.

The process of this invention shall be understood to include the addition of some and up to about 10 wt. % organic acid to the feed and/or periodic contacting of organic acid so as to ensure that the organic acid in the membrane does not become depleted. This added organic acid may be in the form of free organic acid and/or in the form of an ester of the alcohol being separated.

A wide range of polymers may be employed in the process of this invention. An example of a polymer with suitable characteristics is the perfluorinated ionomer Nafion which is produced by Dupont, or the Dow perfluorosulfonate ionomer which is described in U.S. Pat. No. 4,417,969. Nafion ® is a copolymer of perfluoroethylene and perfluorovinylether, the latter component having pendant sulfonic or carboxylic acid groups. The structure of NAFION ® is represented as follows, in the case of the sulfonated NAFION ®:

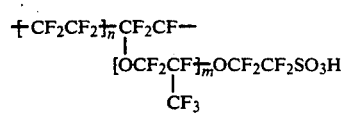

where m=5 to 13.5; n=1,000; and Z=1,2,3 . . .
Equivalent Weight (EW) Ranges 950–1,800.
Cation Exchange Capacity 1.05–0.55 meq/m.

NAFION ® membranes are documented in the literature. (See Hsu and Gierke, *J. Membrane Science,* 13 (1983), 307–326; S. C. Stenson, "Electrolytic Cell Membrane Development Surges", *Chemical and Engineering News,* Mar. 15, 1982; Y. Yamabe, "Perfluorinated Ionomer Membranes," *Kirk-Othmer Encyclopedia of Chemical Technology* (Supplement to 3rd Ed.), John Wiley & Sons, New York, N.Y. (1984); and T. D. Gierke, G. E. Munn and F. C. Wilson, "Morphology of Perfluorosulfonated Membrane Product", pages 195–216 in *Perfluorinated Ionomer Membranes,* edited by A. Eisenberg and H. L. Yaeger, ACS Symposium Series 180 (ACS, Washington, D.C. [1982]; S. J. Sondheimer et al., Rev. Macromol. Chem. Phys., C26(3), 353–413 (1986)

NAFION ® membranes can be symmetric or asymmetric. Asymmetric NAFION ® membranes are comprised of material which is processed so as to produce two membrane sides having different properties such as, for example, a layer of carboxylic acid-containing resin in association with a layer of sulfonic acid-containing resin.

A further example is the zinc salt of sulfonated ethylene-propylene-diene terpolymer designated as Zn-EPDM and described in W. J. MacKnight et al., "The Structure and Properties of Ionomers." *J. Polym. Sc: Macromolecular Rev.,* vol. 16, (1981), pp. 41–122.

The structure of sulfonated EPDM is represented as follows:

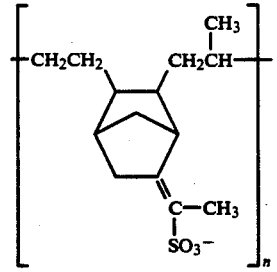

Another class of polymers useful in the present invention are polymers which contain polar groups that can interact with the carboxyl polar group. An example is a chlorosulfonated polyethylene manufactured by Dupont under the tradename Hypalon ®.

Hypalon ® is derived from a polyethylene having a number-average molecular weight of about 20,000. The product contains about 1.5 per cent sulfur and 27.5 per cent chlorine, or approximately one chlorine for each seven carbon atoms and one sulfonyl chloride group for every 90 carbon atoms. All of the sulfur appears in sulfonyl chloride groups, probably attached predominantly to secondary carbon atoms in the chain. The chlorine atoms not attached to sulfur presumably are distributed more or less randomly along the polyethylene chain. Thus, they may occur in primary, secondary, and tertiary positions.

The structure of Hypalon ® may be represented as follows:

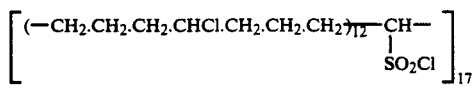

(Golding, B., *Polymers and Resins* (New Jersey, D. Van Nostrand Company, Inc., 1959), p. 388.)

The above are non-limiting examples of polymers that can be employed in the process of this invention.

One method of introducing the organic carboxylic acid into the polymer membrane is to place the membrane in a molten bath of preferably the pure carboxylic acid at 90-160° C.

The period of treatment is the time sufficient to permit the carboxylic acid to dissolve in the membrane, and varies from about 1 hour to about 12 hours depending on temperature. Preferably, sufficient acid is absorbed to comprise approximately 1 to 30 wt. % of the membrane.

Another method of preparing the acid-modified polymer membrane is to introduce the organic carboxylic acid into the polymer before forming the membrane. This can be achieved by dissolving the organic carboxylic acid into the molten polymer or by dissolving both the organic carboxylic acid and polymer in a suitable solvent.

While not wishing to be bound thereby, it is believed that the organic acid of the present invention functions as a plasticizer with respect to the polymer, acting upon polymer structure to enhance selective permeability to alcohols. See in general, J. K. Sears et al., "Plasticizers." *In: Kirk-Othmer Encyclopedia of Chemical Technology* (1982 ed.), vol. 18, pp. 111-183.

The membrane used in the process of the present invention may be utilized in the form of hollow fibers, tubes, films, sheets, etc. The process is conveniently carried out in a diffusion cell which is divided into compartments by means of a membrane or membranes. The compartments will each have means for removing the contents therefrom. The process may be carried out continuously or batchwise, but preferably in a continuous manner.

In practicing the separation of alcohols from acid extract the flow rate of the feed across the membrane surface should be sufficient to prevent undue selectivity loss by concentration polarization. The critical flow will depend on the particular geometry and configuration of the membrane and any supporting or containment vessel used, as well as on temperature. High flux can be achieved by operating with the thinnest membrane that will maintain its physical integrity under the operating conditions. With higher temperatures, lower flow rates can generally be tolerated. Establishing the flow rate which is optimum for any given membrane configuration and set of operating conditions is left to the individual practitioner.

In the process of this invention, alcohol is recovered from an aqueous acid feedstream by contacting the stream against one side of a membrane comprising an organic acid-modified polymer and by withdrawing at a second side of the membrane a permeate comprising alcohol in increased concentration relative to the feedstream.

In one embodiment, the feed is maintained under conditions of pressure such that substantially all of the alcohol is in liquid phase. The permeate is withdrawn in a vacuum, which is generally maintained in the range of 2 to 150 mmHg. The permeated phase is generally withdrawn as a vapor and subsequently condensed. This process is known as "pervaporation".

The vacuum on the permeate side of the membrane can affect both selectivity and flux, with both selectivity and flux generally increasing as the vacuum pressure on the permeate is increased. However, the benefit of increasing the vacuum becomes insignificant at sufficiently low pressures, e.g., less than 2 mm Hg. A lower vacuum can be tolerated at higher temperatures, or with a lower boiling point alcohol (i.e., a lower vacuum can be tolerated with propanol than with butanol).

In another embodiment, a sweep gas is passed across the membrane at a rate sufficient to provide the driving force for permeation of the alcohol. Examples of suitable sweep gases are carbon dioxide, nitrogen, hydrogen, air, or low boiling hydrocarbons such as methane, ethane or propane.

Alternatively, the permeate side of the membrane may be swept by a liquid perstraction solvent in which the permeate is soluble and which is non-corrosive with respect to the membrane, at a rate sufficient to provide a driving force for permeation of the alcohol through the membrane. Examples of perstraction solvents suitable for use in the present invention include aromatic hydrocarbons such as benzene, toluene, xylene, higher molecular weight paraffins, higher molecular weight alcohols, organic acids, and compressed gases, e.g., ethane, propane, butane, etc. Especially preferred perstraction solvents are those which do not form azeotropes with the alcohol, e.g., pentane, ethylbenzene, and long chain high molecular weight alcohols.

The liquid feedstream may be contacted against one side of the membrane in any convenient manner, including continuous, semi-continuous or batchwise operations, in a single or in multiple stages.

The advantage of the present invention may be appreciated by reference to an improved process for the manufacture of alcohols by acid absorption of olefins, the improvement residing in the use of a membrane of the present invention to selectively permeate alcohols from the aqueous strong acid solution thereof co-produced in their synthesis.

Figure 2:
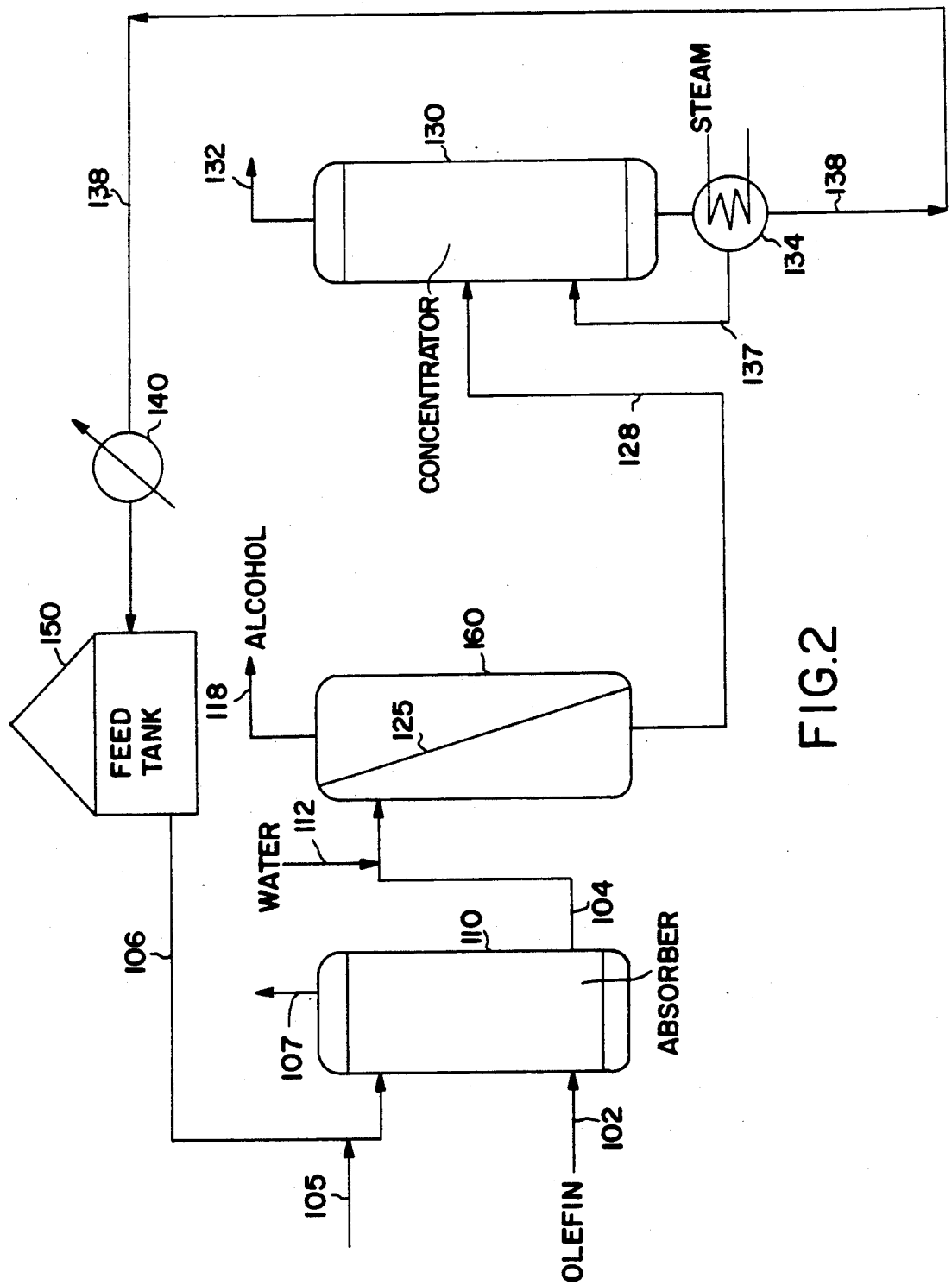
FIG. 2 is a diagrammatic illustration of one embodiment of an improved alcohol recovery process using the process of this invention.

In one embodiment of the process, as illustrated in FIG. 2, butylene feed which is passed via line 102 to absorber 110 is contacted within the absorber by a 55-85 wt. %, preferably 65 to 80 wt. %, sulfuric acid stream 106. Conditions of temperature and pressure are provided sufficient to maintain the resulting sulfuric acid extract in liquid phase, e.g., temperature in the range of 20°-150° C., preferably about 60° C., and pressure in the range of 60-500 psig, preferably about 100 psig. The extract liquid generally comprises from about 45 to 85 wt. % and more preferably from about 60 to 70 wt. % acid strength, and from about 10 to 40 wt. % absorbed butylene values, the balance being water. The extract liquid is withdrawn from the lower portion of absorber 110 via conduit 104. Unabsorbed gas, comprising butylene, is withdrawn from the upper portion of absorber 110 via conduit and can be recycled if desired to conduit 102 or subjected to conventional scrubbing/washing treatment, as with caustic solutions.

Thereafter, water is added to hydrolyze the absorbed olefin values. The extract liquid is passed via line 104 to a mixing zone which can comprise a separate vessel (not shown) or a portion of the conduit 104. In the latter case, water is introduced via conduit 112 directly into conduit 104, and a suitable length of conduit should then be provided to permit the desired complete mixing and reaction of the water with the butyl sulfuric acid extract.

Alternatively, water may be added to a mixing zone in vessel 160 (not shown) wherein suitable means may be provided for adequate mixing of the water with the extract prior to contacting of the resulting diluted acid feedstream against the membrane.

The conditions under which water is added can vary widely. Generally, the temperature of the extract is maintained in the range of about 30°-100° C. The conditions of pressure under which the water is added are not critical, and pressures in the range of 50-500 psig are generally acceptable.

The diluted acid stream thus formed generally has a composition ranging from about A.S. 40-75 wt. % preferably 50-60 wt. %, and E.S. 0.2-1.4, preferably 0.8-1.2 wt. %."A.S." refers to "acid strength", i.e., the concentration of the strong acid in the acid/alcohol feedstream, and "E.S." indicates the "Extract Saturation" of the strong acid solution.

As used herein, the "acid strength" of the acid/alcohol feedstream is defined herein on an organic-free basis as follows, in the illustrative case of $H_2SO_4$:

$$A.S. = \frac{W_1 + \frac{M_1 \times W_4}{M_1 + M_5}}{W_1 + W_2 + \frac{18 W_3}{M_3} + \frac{M_1 \times W_4}{M_1 + M_5}} \times 100$$

wherein $W_1$ is the weight of strong acid, $W_2$ is the weight of $H_2O$, $W_3$ is the weight of alcohol, $W_4$ is the weight of the mono-alkyl ester of the strong acid, $M_3$ is the molecular weight of the alcohol, $M_1$ is the molecular weight of the strong acid, and $M_5$ is the molecular weight of the olefin. Also, the concentrations of the alcohol and alkyl ester in stream 104 can vary widely, and the saturated monoalcohol concentration will generally range from about 5 to 50 wt. % and preferably from about 10 to 40 wt. % and the saturated alcohol alkyl ester of the strong acid will generally range from about 1 to 15 wt. %, and preferably from about 1 to 5 wt. %, of total alkyl ester (mono- and di-alkyl ester).

As used herein, the term "extract saturation" (i.e., "E.S." values) of strong acid solutions, containing alcohol and/or alkyl ester of the strong acid, is defined by the expression (III):

$$E.S. = \frac{{}^1X}{X^A}$$

wherein $X^1$ is the mole fraction of alcohol (and alcohol equivalents represented by the alkyl esters) absorbed in the liquid and $X^A$ is the mole fraction in the liquid of the strong acid and strong acid moieties of the strong acid esters.

The following feedstocks containing secondary butyl ether (SBE), butyl hydrogen sulfate (BuHSO$_4$), sec-butyl alcohol (SBA), sulfuric acid and water are examples of those produced at higher acid concentration with water, and brought to equilibrium:

| | Feed Composition, wt. % | | | | |
|---|---|---|---|---|---|
| | SBE | BuHSO$_4$ | SBA | H$_2$SO$_4$ | H$_2$O |
| A | 0.10 | 0.05 | 6.04 | 40.48 | 53.33 |
| B | 2.88 | 0.27 | 31.36 | 31.14 | 34.34 |
| C | 0.13 | 2.12 | 6.73 | 50.37 | 40.66 |
| D | 3.46 | 10.77 | 32.65 | 30.76 | 22.36 |
| E | 0.14 | 3.19 | 6.87 | 54.09 | 35.72 |
| F | 3.67 | 15.85 | 32.49 | 29.80 | 18.18 |
| G | 0.16 | 6.31 | 6.92 | 62.46 | 24.15 |
| H | 4.13 | 29.78 | 30.79 | 25.91 | 9.39 |

The diluted sulfuric acid stream is then passed to membrane containment vessel 160 which contains therein membrane 125 of the present invention.

The specific design and configuration of the membrane containment vessel will vary according to individual requirements of capacity, flow rate, etc. The vessel should be adapted to support the membrane and to facilitate contacting of the acid stream with a first side of the membrane. Means should also be provided within the vessel for recovery of the permeate and collection of the unpermeated stream. The containment vessel should be equipped with suitable controls for maintaining desired conditions of temperature, pressure, flow rate, etc., with respect to the fluids contained therein. It is preferred that the vessel be adapted to withstand internal pressures of about 50-500 psig; temperatures of about 40°-100° C.; and flux of at least about 50-100 liters/(m$^2$ day); as well as the corrosive action of the acid feedstream.

The membrane may be formed as a flat sheet a first side of which is contacted by the acid feedstream, an alcohol-enriched permeate being recovered at a second side of the membrane. Alternatively, the membrane may comprise a hollow tube around or through which the feedstream is passed, with the permeate being collected at the inner or outer surface of the membrane, respectively.

The liquid feedstream may be contacted against one side of the membrane in any convenient manner, including continuous, semi-continuous or batchwise operations, in a single or in multiple stages.

In one embodiment of the process a vacuum is maintained at the second side of the membrane at about 0.2 psia. The diluted acid feedstream containing alcohol is contacted against one side of the membrane, and a vapor-phase permeate comprising alcohol in increased concentration relative to the feedstream is withdrawn at the second side of the membrane.

Advantageously, where the permeate is collected by pervaporation through the membrane, the heat of reaction during olefin hydration and hydrolysis of the absorbed olefin values would supply at least a part of the heat required to maintain the temperature of the permeate as it pervaporates through the membrane.

. The permeate, which preferably contains at least about 60 wt. % alcohol, may then be pressed via line 118 for further conventional processing, e.g., to remove excess water, and for separation from residual hydrocarbons.

As illustrated in FIG. 2, the alcohol-depleted diluted acid stream which is thereby recovered at the feed side of the membrane, exits membrane containment vessel 160 via line 128 and is passed to acid concentrator 130 for reconcentration by distillation (e.g., using steam heat exchanger 134 and reboiled stream 137) for removal of water as overhead 132 and to form a second bottoms product 138 comprising a reconcentrated acid stream suitable for recycling in the process. The concentrated bottoms are cooled in cooler 140 and passed to storage tank 150 for ultimate recycle to the absorption step 110, with addition of make-up acid 105, as required.

The process illustrated in FIG. 2 achieves an energy savings relative to conventional processes which are characterized by the energy costly process step of steam stripping of the diluted acid feedstream to obtain an overhead alcohol-containing fraction and a diluted sulfuric acid bottoms product.

In another embodiment of the process of this invention, the membrane used is characterized by selectivity values with respect to the components of the diluted acid solution such that alcohol and sufficient water permeate through the membrane to form an aqueous permeate comprising alcohol in increased concentration relative to the feed, so that there is thereby also recovered at the feed side of the membrane an acid solution which is substantially depleted of alcohol and which is reconstructed with respect to acid content to a concentration suitable for direct recycle in the process.

Figure 3:
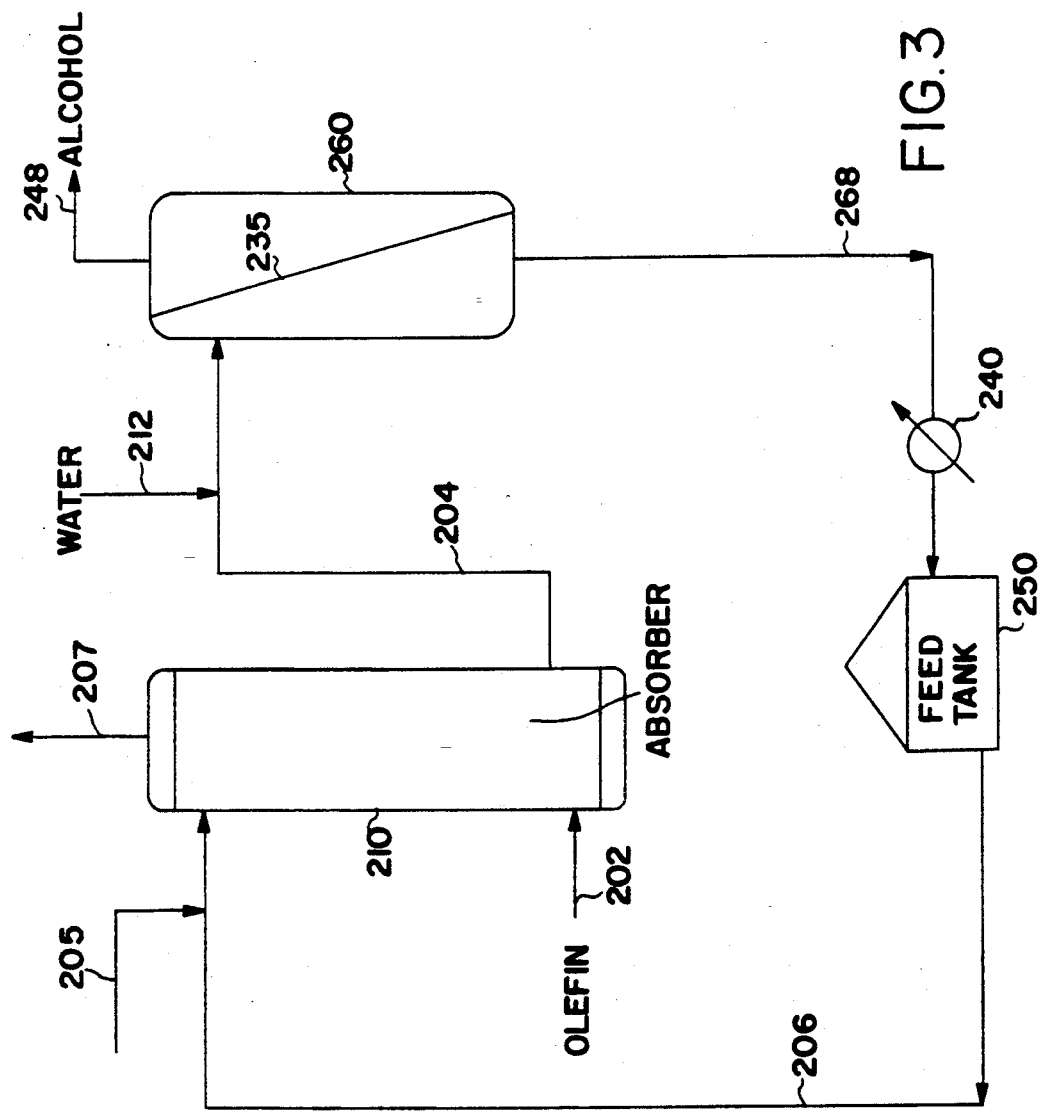
FIG. 3 is a diagrammatic illustration of a second embodiment of the process of this invention.

As illustrated in FIG. 3, butylene feed is passed via line 202 to absorber 210 for contacting within the absorber by a 55-85 wt. %, and preferably 65 to 80 wt. %, sulfuric acid stream from line 206. Similar conditions of temperature and pressure as in the previous embodiment are contemplated, i.e. temperature in the range of 20°-150° C. and pressure in the range of 60-500 psig. The extract liquid is withdrawn from the lower portion of absorber 210 via conduit 204. Unabsorbed gases are withdrawn from the upper portion of absorber 210 through conduit 207; and may be recycled to conduit 202 or treated conventionally by scrubbing or washing.

The liquid stream from the absorbing zone is passed via line 204 to a mixing zone (as shown, a portion of the conduit 204). Water is introduced into conduit 204 via conduit 212.

The resulting diluted acid stream is then introduced into membrane containment vessel 260 and is contacted against a first side of membrane 235. According to this embodiment, an aqueous permeate containing alcohol permeates membrane 235 and exits the membrane containment vessel via line 248.

An aqueous concentrated strong acid solution is thereby formed of about 55 to 85 wt. %, and preferably 55 to 65 wt. % acid strength. This solution is passed via line 268 to feed tank 250 where it may be stored for eventual recycle in the process via line 206 to absorber 210, with addition of make-up acid 205, as necessary.

The alcohol-containing permeate is then passed via line 248 to a distillation tower and other conventional separations apparatus, or alternatively, is contacted against one or more membranes known in the art to be effective to separate alcohol from water or residual hydrocarbons, such as the Nafion membrane of Dupont, so as to enable recovery of the alcohol product.

The process of this invention which is illustrated in FIG. 3 achieves energy credits relative to conventional processes which require both steam stripping and acid reconcentration by distillation.

In a preferred embodiment of the present invention, a continuous low-energy process for the manufacture and recovery of alcohols is provided using a "membrane reactor unit" comprising a membrane of the present invention.

According to the process, the removal of alcohol from the liquid extract stream from the absorber, by permeation of the alcohol through the membrane of the membrane reactor unit, drives the reaction which is represented in Reaction I above, toward further absorption of the olefin in acid to form absorbed olefin values. Thus as the liquid extract stream from the absorber is contacted against a first side of the membrane, and the alcohol is removed from the extract stream by permeation through the membrane, the reaction by which olefin in the extract stream is absorbed in aqueous strong acid is driven to proceed at a rate sufficient to maintain substantially in equilibrium the liquid extract stream from the absorber with the unpermeated acid solution recovered at the first side of the membrane by permeation of the alcohol.

Since the acid-catalyzed absorption of the olefin is continuously driven by removal of the alcohol, a less concentrated aqueous strong acid may be used for absorption than was recited herein for use in the prior art processes. The aqueous concentrated strong acid used in the present process will generally comprise from about 35 to 70 wt. %, and preferably 40 to 65 wt. %, acid strength strong acid for hydration of, e.g. butylene.

In addition, since in this embodiment it is preferred that the water of hydrolysis be added to the liquid extract stream in an amount not substantially in excess of the amount sufficient to form such alcohol as will permeate the membrane, under the given conditions of flux through the membrane, and to compensate for water lost by copermeation through the membrane, flow rate of the liquid extract stream, and flux through the membrane, there is thereby avoided the acid dilution which characterizes conventional processes, and the consequent requirement for reconcentration of the acid before reacting to achieve a concentration suitable for reuse in the process.

The process achieves substantial energy savings relative to conventional alcohol manufacture and recovery processes which are characterized by the energy-intensive steps of alcohol steam-stripping and acid reconcentration. In addition, the present process improves over prior art processes which require the presence in the extract mixture of water in excess (which in prior art processes is for the purpose of diluting the acid extract to facilitate recovery of the alcohol therefrom by steam stripping). In the present process water is added stoichiometrically to form such alcohol as will permeate the membrane, and compensate for water lost by any copermeation through the membrane. Thus there is thereby avoided a shifting of the Reaction I equilibrium back to formation of the olefin and free acid which occurs in the presence of excess water.

The "membrane reactor unit" comprises one or more membranes of the present invention supported within a containment vessel which is adapted to facilitate: (1) the contacting of the liquid extract stream from the absorber with a first side of the membrane; (2) the recovery at the second side of the membrane of the permeated alcohol; and (3) the collection of the unpermeated aqueous acid solution at the first side of the membrane.

The function of the membrane reactor unit is to enable continuous removal of the equilibrium-limiting product in Reaction I above, the alcohol, so as to drive the reaction by which olefin is absorbed by aqueous strong acid toward continued formation of absorbed olefin values.

The containment vessel will preferably comprise an inlet means for introduction of the liquid extract stream containing alcohol into a first zone of the vessel; means for supporting the membrane within the vessel; a second zone of the vessel, the second zone being separated from the first zone by a membrane of the present invention; an outlet means from said second zone for recovery of the permeated alcohol; and an outlet means from said first zone for collection of the unpermeated aqueous acid solution. The vessel should be equipped with suitable controls for regulating flow rate, temperature and pressure with respect to the fluids contained therein.

Preferably the process is performed such that as alcohol is formed by hydrolysis of absorbed olefin values, the alcohol permeates the membrane, thereby facilitating recovery at the first side of the membrane of an unpermeated aqueous solution substantially in equilibrium with the liquid stream from the absorbing zone.

Figure 4:
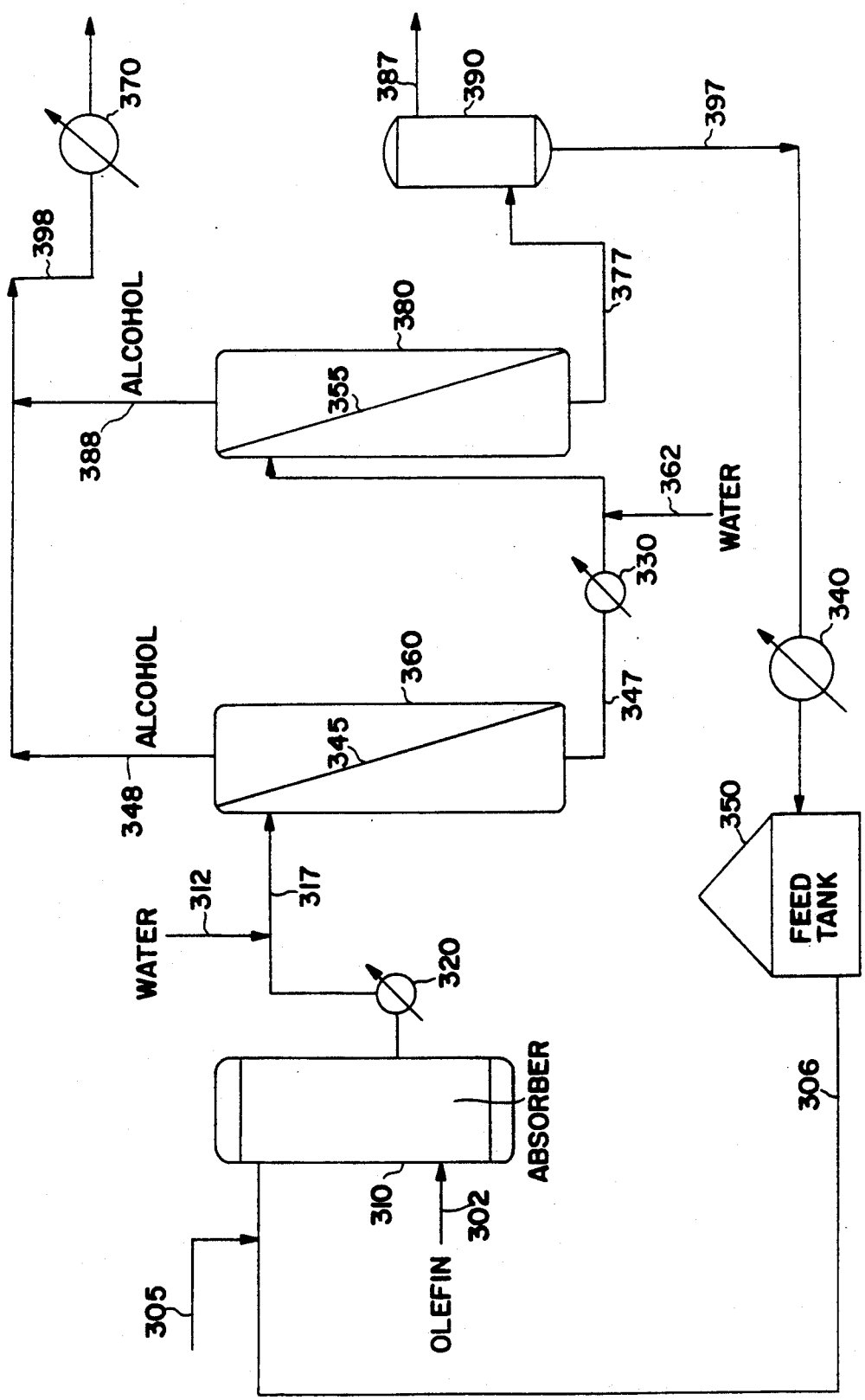
FIG. 4 is a diagrammatic illustration of a preferred embodiment of the process of this invention.

As illustrated in FIG. 4, hydrocarbon feed containing olefin such as, e.g., butylene, is introduced via line 302 into absorber 310, for contacting with aqueous concentrated strong acid, such as sulfuric acid from line 306. When sulfuric acid is used as the strong acid, stream 306 will generally contain from about 35 to 70 wt. %, and preferably 40 to 65 wt. %, acid strength sulfuric acid for hydration of the butylene. There may be present in the feed, in addition to the olefin, inert paraffins derived from the cracking of petroleum hydrocarbons to form olefins. It is preferred that the olefin comprise at least about 30 wt. % of the feed. Mixers (not shown) may optionally be used in the absorber to insure that the acid and hydrocarbon are well mixed and preferably at least partially emulsified.

The temperature and pressure employed in absorber 310 generally range from about 20° C. to 150° C. and about 100 to 500 psig, respectively. Preferably, the pressure within the absorber is sufficient to maintain the hydrocarbon feed in liquid phase.

The resulting liquid stream which is withdrawn as a liquid product via line 317 from absorber 310 contains water (preferably about 20 to 30 wt. %), sulfuric acid (preferably, in concentration of about 60 wt. % acid strength), and about 20 to 30 wt. % absorbed olefin values and unreacted hydrocarbons, such as paraffins and tars. Thus the acid stream thus formed would have a composition of about S.S. 60 wt. % and E.S. 0.8. The liquid stream is then passed via lien 317 to membrane reactor unit 360 comprising membrane 345 of the present invention.

Prior to contacting with the membrane, the liquid stream from the absorber comprising sulfuric acid extract and unreacted hydrocarbons is admixed with water to hydrolyze at least a portion of the absorbed olefin values. The water may be added by in-line addition via line 312 (as shown) to the liquid stream prior to introduction of the stream into the membrane reactor unit or alternatively by introduction into a zone within the membrane reactor unit or within a separate vessel (not shown).

It is preferred that water be added as required in an amount not substantially in excess of the amount sufficient to: (1) form such alcohol as will permeate the membrane under the given conditions of flux; and (2) compensate for any water lost by co-permeation with the alcohol through the membrane, in order that the composition of the liquid stream from the absorbing zone and the unpermeated aqueous acid solution recovered at the first side of the membrane by permeation of the alcohol are maintained substantially in equilibrium.

Advantageously, where the alcohol permeate is collected by pervaporation through the membrane, the heat of reaction during olefin hydration would supply at least a part of the heat required to maintain the temperature of the permeate as it pervaporates through the membrane. Heat exchanger 320 is provided to add or remove heat from the liquid before it contacts the membrane. Optionally, or in the alternative, a heat exchanger may be provided in line 317 after addition of water to the liquid stream.

Various configurations of the membrane and the membrane reactor unit are possible, depending on desired conditions of temperature, flux, pressure, etc. The use of a hollow fiber membrane is preferred since de-emulsification of the liquid stream during passage through the hollow fibers would be more difficult than through either plate-and-frame or spiral wound modules.

In FIG. 4, the alcohol is recovered as an overheat product via line 348 by vapor phase pervaporation through membrane 345. The overhead alcohol product can then be passed via line 398 for condensation to heat exchanger 310 and for further conventional processing, for example, to remove water copermeated with the alcohol.

The unpermeated aqueous acid solution is withdrawn from membrane reactor unit 360 through line 347.

In FIG. 4, the aqueous acid solution in line 347 comprising absorbed butylene values as well as unreacted hydrocarbons is passed to a second membrane reactor unit 380 containing membrane 355 of the present invention. Optionally, mixers (not shown) may be used to insure that the solution remains emulsified. Heat exchanger 330 is provided to add or remove heat from the liquid before it contacts membrane 355. As before, where the alcohol is to be pervaporated through the membrane, the heat of reaction of the continuing hydration of the olefin would supply at least part of the heat needed to maintain the temperature of the permeate as it pervaporates through the membrane.

Water is added via line 362 to hydrolyze absorbed olefin values.

The alcohol permeate is recovered from membrane reactor unit 380 as an overheat product through line 388. The alcohol is then passed to line 398 for cooling using heat exchanger 370, and further conventional processing.

The effluent from membrane reactor unit 380 which is withdrawn through line 377 contains predominantly two phases: a spent hydrocarbon phase comprising, e.g., butanes, butadienes, and tars and oils formed by polymerization reactions; and a sulfuric acid extract phase comprising sulfuric acid and residual absorbed olefin values including alcohol. The effluent is passed to phase separator 390 for conventional separation of the two phases and removal via line 387 of the spent hydrocarbon phase. A bottoms portion comprising the sulfuric acid phase is passed via line 397 for recycling in the process. Generally this phase comprises about 7 to 17 wt. % alcohol and about 40 to 65 wt. % sulfuric acid. Heat exchanger 340 is provided to add or remove heat from the acid extract before it is passed to feed tank 350 for recycling in the process.

The acid extract, not having been substantially diluted in the process, is suitable for reuse directly to the absorber. Make-up sulfuric acid may be provided to the absorber via line 305.

It will be obvious that various changes and modifications may be made without departing from the invention and it is intended, therefore, that all matter contained in the foregoing description shall be interpreted as illustrative only and not limitative of the invention.

In the following examples, a membrane sample approximately 5.5 cm in diameter was prepared for mounting in a test cell of a laboratory pervaporization unit. A liquid feed comprising (unless otherwise indicated) 16.5 wt. % SBA, 50.2 wt. % $H_2SO_4$ and 33.3 wt. % $H_2O$ was pumped at atmospheric pressure over the surface of the membrane at a rate of about 3 liters per minute. The permeate was withdrawn under vacuum of about 150 kPa. The vapor-phase permeate was then condensed on a glass cold trap cooled by liquid nitrogen. The condensate was warmed to room temperature, and the amount of water in the condensate was determined by a Karl Fischer filtration. During a test of the membrane, the permeate was sampled at hourly intervals and analyzed for water content by gas chromatography.

pH measurements confirmed that sulfuric acid was not present in measurable quantity either in the permeate sample or on the permeate side of the membrane surface.

EXAMPLE 1

| NAFION ® - 115 84-1012 Treated with Isostearic Acid* (125 μm Thick, 1,100 $SO_3H$ Equivalent Weight) | | | |
|---|---|---|---|
| | | Permeate | |
| Elapsed Time Hrs | Temperature °C. | Flux kg/(m²d) | SBA wt. % |
| 1 | 50.0 | 2.0 | 85.5 |
| 1 | 70.0 | 4.3 | 87.3 |
| 3 | | 4.0 | 87.5 |
| 4 | | 7.0 | 83.9 |
| (Test restarted) | | | |
| 1 | 70.0 | 6.0 | 86.4 |
| 2 | | 10.3 | 80.3 |
| 3 | | 10.8 | 80.3 |

*Preparation: The NAFION ® membrane was heated in pure isostearic acid to 150° C. for one hour. Both the membrane and the acid turned black at about 85° C. The membrane was left in the acid at room temperature until use four days later. A slight amount of swelling was evident. The membrane was then mounted in the pervaporation unit. Good selectivity for the alcohol is evidenced by the data on weight percent alcohol in the permeate from a feed comprising 16.5 wt. % alcohol.

EXAMPLES 2-4

Three polymer solutions of zinc sulfonated ethylene-propylene-diene (Zn-EPDM) were prepared by adding 15% by weight Zn-EPDM polymer to a 5/95 wt. % mixture of methanol:toluene. After complete mixing, isostearic acid was added and mixed. One sample of the prepared membrane (Example 2) contained 10.3 wt. %, by polymer weight, isostearic acid. Another sample contained 15 wt. % by polymer weight, isostearic acid (Example 3): and a third sample (Example 4) contained 25 wt. % by polymer weight isostearic acid. The membranes were all cast on separate sheets of Celgard 2400 film and air dried overnight.

Each membrane was then mounted in turn in the pervaporation unit.

EXAMPLE 2

| Zn-EPDM Containing 10 wt. % ISA | | | |
|---|---|---|---|
| | | Permeate | |
| Elapsed Time Hrs | Temperature °C. | Flux kg/(m²d) | SBA wt. % |
| 2 | 80.0 | 8.8 | 82.2 |
| 3 | | 11.0 | 80.5 |
| 4 | | 10.5 | 77.4 |
| 5 | | 9.8 | 74.5 |
| 6 | | 5.5 | 42.2 |

EXAMPLE 3

| Zn-EPDM Containing 15 wt. % Isostearic Acid | | | |
|---|---|---|---|
| | | Permeate | |
| Elapsed Time Hrs | Temperature °C. | Flux kg/(m²d) | SBA wt. % |
| 1 | 80.0 | 4.5 | 84.2 |
| 2 | | 14.8 | 79.7 |
| 3 | | 11.8 | 78.5 |
| (Test restarted) | | | |
| 1 | 80.0 | 10.3 | 77.7 |
| 2 | | 11.4 | 78.1 |
| 3 | | 9.3 | 75.0 |
| 4 | | 7.5 | 73.6 |
| 5 | | 5.5 | 44.4 |
| 6 | | 5.3 | 37.3 |

Selectivity declined markedly in the fourth hour of the second flux, possibly due to deterioration of the membrane in the sulfuric acid environment.

EXAMPLE 4

| Zn-EPDM Containing 25 wt. % Isostearic Acid | | | |
|---|---|---|---|
| | | Permeate | |
| Elapsed Time Hrs | Temperature °C. | Flux kg/(m²d) | SBA wt. % |
| 1 | 50.0 | 4.0 | 83.5 |
| 2 | 70.0 | 11.5 | 83.2 |
| 3 | | 11.0 | 82.9 |
| 4 | | 10.3 | 82.6 |
| 5 (Restarted) | | 9.0 | 82.4 |
| 6 | | 10.0 | 80.9 |
| 7 | | 8.8 | 80.2 |
| 8 (Restarted) | | 7.5 | 80.2 |
| 9 | | 7.0 | 79.7 |
| 10 | | 6.8 | 73.0 |
| 11 | | 6.3 | 76.4 |
| 12 | | 6.5 | 38.0 |
| 13 | | 6.5 | 38.0 |
| 14 | | 6.0 | 69.8 |
| Add 20 g ISA to feed (2.5 wt. % of total Feed) | | | |
| 15 | | 6.0 | 75.8 |
| 16 | | 6.8 | 80.6 |
| 17 | | 6.0 | 81.8 |

Addition of isostearic acid to the feed appeared to improve selectivity of the membrane for the alcohol.

EXAMPLE 5

| Lower SBA Concentration* | | | |
|---|---|---|---|
| | | Permeate | |
| Elapsed Time Hrs | Temperature °C. | Flux kg/(m²d) | SBA wt. % |
| 1 | 70.0 | 5.0 | 75.2 |
| 2 | | 5.3 | 76.8 |
| 3 | | 4.3 | 76.5 |
| 4 | | 4.3 | 71.9 |

-continued

| Lower SBA Concentration* | | | |
|---|---|---|---|
| | | Permeate | |
| Elapsed Time Hrs | Temperature °C. | Flux kg/(m²d) | SBA wt. % |
| 5 | | 3.5 | 72.4 |

*Preparation: A fresh piece of the membrane used in Example 4 was mounted and tested using a 7 wt. % SBA, 50 wt. % H₂SO₄, 43 wt. % H₂O feed solution. Samples of the permeate were collected in liquid nitrogen.

EXAMPLE 6

| Hypalon ® - Chlorinated Polyethylene - 16 wt. % ISA* | | | |
|---|---|---|---|
| | | Permeate | |
| Elapsed Time Hrs | Temperature °C. | Flux kg/(m²d) | SBA wt. % |
| 1 | 70.0 | 4.3 | 20.4 |
| 2 | | 5.3 | 46.4 |
| 3 | 80.0 | 5.5 | 72.3 |
| 4 | | 5.8 | 71.0 |
| 5 | | 4.5 | 71.0 |
| 6 | | 3.5 | 48.4 |
| 7 | | 3.0 | 17.3 |

*Preparation: A membrane was prepared from DuPont Hypalon ®, a chlorinated polyethylene having composition 24% chlorine and 1% sulfur. 15 wt. % polymer was added to a solution comprising 5 wt. % methanol and 95 wt. % toluene. Isostearic acid was added to the resulting solution in an amount to yield 16% ISA by polymer weight. After mixing, the membrane was cast on celgard 2400 film and then left overnight to dry.

What is claimed is:

1. In the process for preparing a saturated monoalcohol having from 2 to 8 carbon atoms per molecule by the conventional steps of absorbing the corresponding olefin into an aqueous concentrated strong inorganic acid thereby forming an alkyl ester of said acid corresponding to said olefin, recovering a liquid phase containing said acid alkyl ester, and contacting said recovered liquid phase with water thereby liberating said alcohol in the resulting product solution; the improvement comprising the steps of: (a) contacting the product solution containing said liberated alcohol against a first side of an organic acid-modified polymer membrane, and (b) withdrawing at a second side of the membrane a permeate of said alcohol solution having an increased concentration of alcohol relative to said product solution, thereby recovering at the first side of the membrane a diluted strong inorganic acid solution, said diluted acid solution being substantially depleted of said alcohol.

2. The process of claim 1 wherein said strong inorganic acid is sulfuric acid.

3. Process of claim 2 wherein the said diluted sulfuric acid solution contains from about 45 to 85 wt. % acid strength sulfuric acid.

4. The process of claim 2 wherein the alcohol recovered is sec-butyl alcohol and the feed from which the alcohol is recovered comprises sec-butyl alcohol, sulfuric acid and water.

5. The process of claim 2 wherein the alcohol is isopropyl alcohol and the feed from which the alcohol is recovered comprises isopropyl alcohol, sulfuric acid and water.

6. Process of claim 2 wherein the organic acid is selected from the group consisting of carboxylic acids having from 6 to 20 carbon atoms per molecule.

7. Process of claim 6 wherein the organic acid is isostearic acid.

8. Process of claim 6 wherein the organic acid comprises about 1 to 30 wt. % of the membrane.

9. Process of claim 2 wherein the feed mixture additionally contains some and up to about ten wt. % of the organic acid.

10. The process of claim 2 wherein the membrane is prepared by contacting the membrane with the organic acid at a temperature and for a time sufficient for absorption of at least a portion of the acid by the membrane.

11. The process of claim 2 wherein the membrane is prepared by contacting the polymer with the organic acid to form a mixture and therefore heating said mixture at a temperature and for a time sufficient for formation of a membrane comprising said polymer and at least a portion of said organic acid.

12. The process of claim 2 wherein the membrane comprises a copolymer of perfluoroethylene and perfluorovinylether wherein the perfluorovinylether moiety bears pendant sulfonic acid groups, and the acid is isostearic acid.

13. The process of claim 12 wherein the alcohol recovered is sec-butyl alcohol and the feed from which the alcohol is recovered comprises sec-butyl alcohol, sulfuric acid and water.

14. The process of claim 12 wherein the alcohol recovered is isopropyl alcohol and the feed from which the alcohol is recovered comprises isopropyl alcohol, sulfuric acid and water.

15. The process or claim 2 wherein the membrane comprises chlorosulfonated polyethylene.

16. The process of claim 2 wherein the membrane comprises zinc sulfonated ethylene-propylene-diene.

17. The process of claim 1 wherein the membrane comprises the following copolymer:

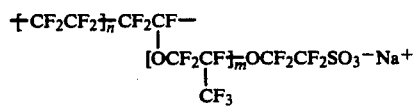

where m=5 to 13.5; n=1,000.

18. The process of claim 2 wherein the permeate is withdrawn at a pressure which is less than the pressure which is maintained on the feed.

19. The process of claim 18 wherein the permeate is withdrawn at a partial pressure which is less than atmospheric pressure.

20. The process of claim 19 wherein the permeate is withdrawn as a vapor.

21. The process of claim 2 wherein a gas is swept against the second side of the membrane, the permeate vaporizing in said gas.

22. Process of claim 2 wherein a liquid solvent is passed against the second side of the membrane, the permeate being soluble in said liquid solvent.

* * * * *